US 10,335,618 B2

(12) United States Patent
Zhou et al.

(10) Patent No.: US 10,335,618 B2
(45) Date of Patent: Jul. 2, 2019

(54) BREATHING APPARATUS WITH ULTRAVIOLET LIGHT EMITTING DIODE

(71) Applicants: Ling Zhou, Dublin, CA (US); Fang Hu, Dublin, CA (US)

(72) Inventors: Ling Zhou, Dublin, CA (US); Fang Hu, Dublin, CA (US)

( * ) Notice: Subject to any disclaimer, the term of this patent is extended or adjusted under 35 U.S.C. 154(b) by 595 days.

(21) Appl. No.: 14/323,778

(22) Filed: Jul. 3, 2014

(65) Prior Publication Data
US 2016/0001108 A1    Jan. 7, 2016

(51) Int. Cl.
*A62B 18/02*   (2006.01)
*A62B 7/10*    (2006.01)
*A62B 18/10*   (2006.01)
*A61L 9/20*    (2006.01)
*A41D 13/11*   (2006.01)
*A61L 2/00*    (2006.01)
*A61L 9/00*    (2006.01)

(52) U.S. Cl.
CPC .......... *A62B 18/02* (2013.01); *A41D 13/1192* (2013.01); *A61L 2/00* (2013.01); *A61L 9/00* (2013.01); *A61L 9/20* (2013.01); *A62B 7/10* (2013.01); *A62B 18/025* (2013.01); *A62B 18/10* (2013.01)

(58) Field of Classification Search
CPC .. A62B 7/00; A62B 7/10; A62B 18/02; A62B 18/025; A62B 23/00; A62B 23/02; A62B 23/025; A62B 23/04; A62B 23/06; A61L 9/20; A41D 13/11; A41D 13/1192
See application file for complete search history.

(56) References Cited

U.S. PATENT DOCUMENTS 5,165,395 A * 11/1992  Ricci ................. A41D 13/1146
                                                128/202.22
5,698,866 A * 12/1997  Doiron .................. A61N 5/062
                                                     257/717
(Continued)

FOREIGN PATENT DOCUMENTS

CN      102763917 A  * 11/2012  ......... A41D 13/1192
JP      2010523190 A    7/2010
WO      2012151204 A1  11/2012

OTHER PUBLICATIONS

EPO, "Communication pursuant to Rule 164(1) EPC", partial search report, dated Jan. 25, 2018, 12 pages.
(Continued)

*Primary Examiner* — LaToya M Louis
(74) *Attorney, Agent, or Firm* — Patent Law Group LLP; David C. Hsia

(57) ABSTRACT

A breathing apparatus according to embodiments of the invention includes a facemask portion sized to cover a lower portion of a wearer's face. The facemask portion includes a flow chamber. The flow chamber includes a first opening disposed near a first end of the flow chamber, a second opening disposed near a second end of the flow chamber, and a serpentine passage disposed between the first opening and the second opening. At least one light emitting diode configured to emit light having a peak wavelength in the ultraviolet range is disposed in the serpentine passage. The at least one light emitting diode is disposed off center relative to a centerline oriented along a direction of air flow through the serpentine passage.

16 Claims, 9 Drawing Sheets

(56) References Cited

U.S. PATENT DOCUMENTS

| | | | |
|---|---|---|---|
| 8,733,356 B1 | 5/2014 | Roth | |
| 2004/0007234 A1* | 1/2004 | Duxbury | A62B 23/06 |
| | | | 128/205.27 |
| 2005/0229929 A1* | 10/2005 | Ivri | A61M 11/005 |
| | | | 128/203.12 |
| 2005/0242013 A1 | 11/2005 | Hunter et al. | |
| 2007/0101867 A1* | 5/2007 | Hunter | A61L 9/205 |
| | | | 96/224 |
| 2007/0163588 A1* | 7/2007 | Hebrank | A61L 9/16 |
| | | | 128/204.18 |
| 2009/0190349 A1* | 7/2009 | Middlemass | G02B 6/4296 |
| | | | 362/240 |
| 2009/0205664 A1* | 8/2009 | Lyon | A61L 2/10 |
| | | | 128/205.12 |
| 2009/0277451 A1* | 11/2009 | Weinberg | A41D 13/1176 |
| | | | 128/206.14 |
| 2010/0175694 A1 | 7/2010 | James et al. | |
| 2012/0279503 A1* | 11/2012 | Zhou | A41D 13/1192 |
| | | | 128/205.27 |
| 2013/0146052 A1* | 6/2013 | Ding | B01D 46/0086 |
| | | | 128/202.22 |

OTHER PUBLICATIONS

JP 2016-576045, "First Office Action," dated Dec. 20, 2017, 8 pages.
PCT/US2015/034731, "International Search Report and Written Opinion," 11 pages.
EP 15815097.9 Extended EP Search Report.
JP 2016-576045, "Final Office Action" dated Aug. 6, 2018, 4 pages.
EP Application No. 15815097.9, Article 94(3) Office Action dated Jan. 30, 2019.

\* cited by examiner

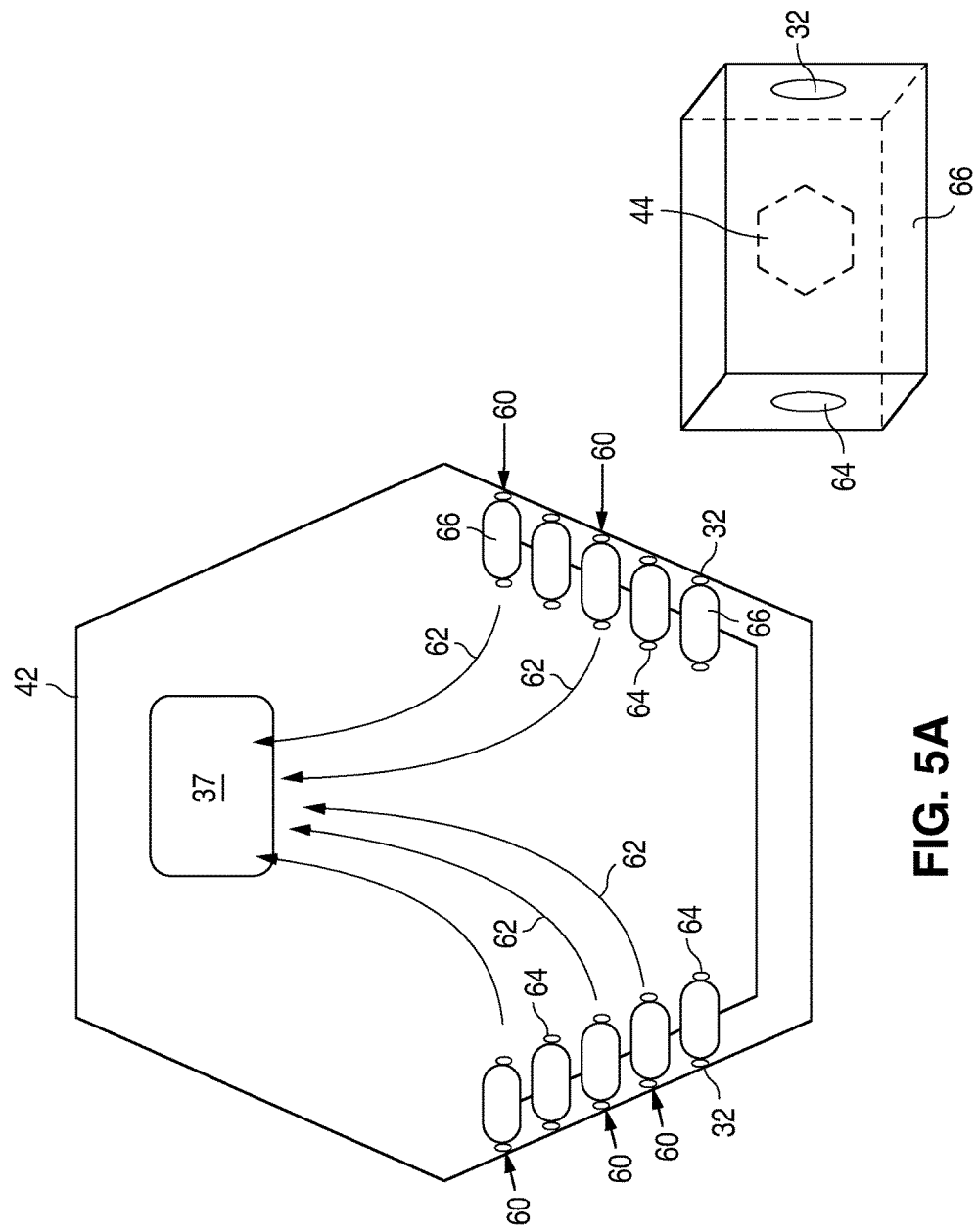

BREATHING APPARATUS WITH ULTRAVIOLET LIGHT EMITTING DIODE

BACKGROUND

Field of Invention

The present invention relates to a breathing apparatus that uses ultraviolet light emitting diodes to reduce risk from airborne pathogens.

Description of Related Art

Acute respiratory infection (ARI), which causes millions deaths every year, is the number one cause of death in the developing world, and number three cause of death worldwide. In the event of an ARI pandemic or other emerging respiratory disease such as severe acute respiratory syndrome (SARS), measures are preferably taken immediately to reduce the infection rate, rather than wait for a targeted vaccine or antiviral drug to be developed. Wearing a facemask is a widely accepted, non-pharmaceutical method to reduce the risk of respiratory infection.

Examples of common facemasks include disposable surgical facemasks and N95 respirators. This type of facemask reduces transmission of airborne pathogens by preventing a person from directly touching his nose and mouth with dirty hands and by containing large liquid droplets expelled during sneezing or coughing. This type of facemask is unable to disinfect the air being inhaled or exhaled, and typically cannot block airborne viruses, most of which are smaller than 0.3 microns and can pass through the pores in the fabrics of this type of facemask. In addition, because the main air passageway of the facemask is blocked by one or more layers of fabric, this type of facemask is generally uncomfortable to wear, which may discourage people from using facemasks. Furthermore, if the mask is not face-fitted, a significant amount of air can leak through the periphery of the mask, significantly reducing the mask's effectiveness and leading to other inconveniences such as fogging of lenses in cold weather for eye-glass wearers from leakage of moist air.

FIG. 1 illustrates a chemical and biological protection mask described in more detail in US 2010/0132715. The gas mask assembly 2 generally comprises a molded mask portion 10 containing a frontal one-way exhalation valve 20 and one or more adjacent inhalation apertures 12. The inhalation aperture 12 is equipped with a push-and-twist receptacle 14. A UV-illumination tube 50 is interposed between the inhalation aperture 12 and a filter assembly 40, which may provide mechanical filtration capabilities, such as HEPA-type or charcoal filters. The UV illumination tube 50 is a short multi-part cylinder, approximately 2-5", with mating push-and-twist receptacle/seats at each end for seating the filter assembly 40 and insertion into receptacle 14 of mask 10. The UV illumination tube 50 further comprises a cylindrical aluminum outer shell, and a cylindrical plastic insert that seats a plurality of elongate axially-aligned circuit boards each carrying a plurality of surface-mounted LED UV lights disposed inwardly toward the centerline of the tube 50. The UV illumination tube 50 is centrally unobstructed and incoming air from filter assembly 40 remains free to pass into the inhalation aperture 12 of the mask 10. While passing through the tube's length, the air is illuminated with high-intensity shortwave ultraviolet light from the LEDs and is thereby fully filtered and irradiated for combined chemical and biological protection. Power for the LEDs is derived from an on-board battery which may be built into the UV illumination tube 50 or the mask 10 (requiring slide-connectors along the lip of the tube 50), and/or from a solar cell likewise mounted on the UV illumination tube 50 or the mask 10. Preferably, an on/off detent switch 52 for the LEDs is provided on the tube 50 as well.

SUMMARY

A breathing apparatus according to embodiments of the invention includes a facemask portion sized to cover a lower portion of a wearer's face. The facemask portion includes a flow chamber including a first opening disposed near a first end of the flow chamber and a second opening disposed near a second end of the flow chamber. At least one light emitting diode configured to emit light having a peak wavelength in the ultraviolet range is disposed between the first opening and the second opening in the flow chamber. The flow chamber has a volume no more than 80 cm$^3$.

A breathing apparatus according to embodiments of the invention includes a facemask portion sized to cover a lower portion of a wearer's face. The facemask portion includes a flow chamber. The flow chamber includes a first opening disposed near a first end of the flow chamber, a second opening disposed near a second end of the flow chamber, and a serpentine passage disposed between the first opening and the second opening. At least one light emitting diode configured to emit light having a peak wavelength in the ultraviolet range is disposed in the serpentine passage. At least one light emitting diode is disposed off center relative to a centerline oriented along a direction of air flow through the serpentine passage.

BRIEF DESCRIPTION OF THE DRAWINGS

FIG. 5A illustrates an alternative example of a support layer and air flow through a flow chamber in the facemask illustrated in FIG. 2. FIG. 5B illustrates an individual reflective chamber.

FIG. 7 is a plot of air pressure and UV LED drive current as a function of time.

DETAILED DESCRIPTION

Figure 2:
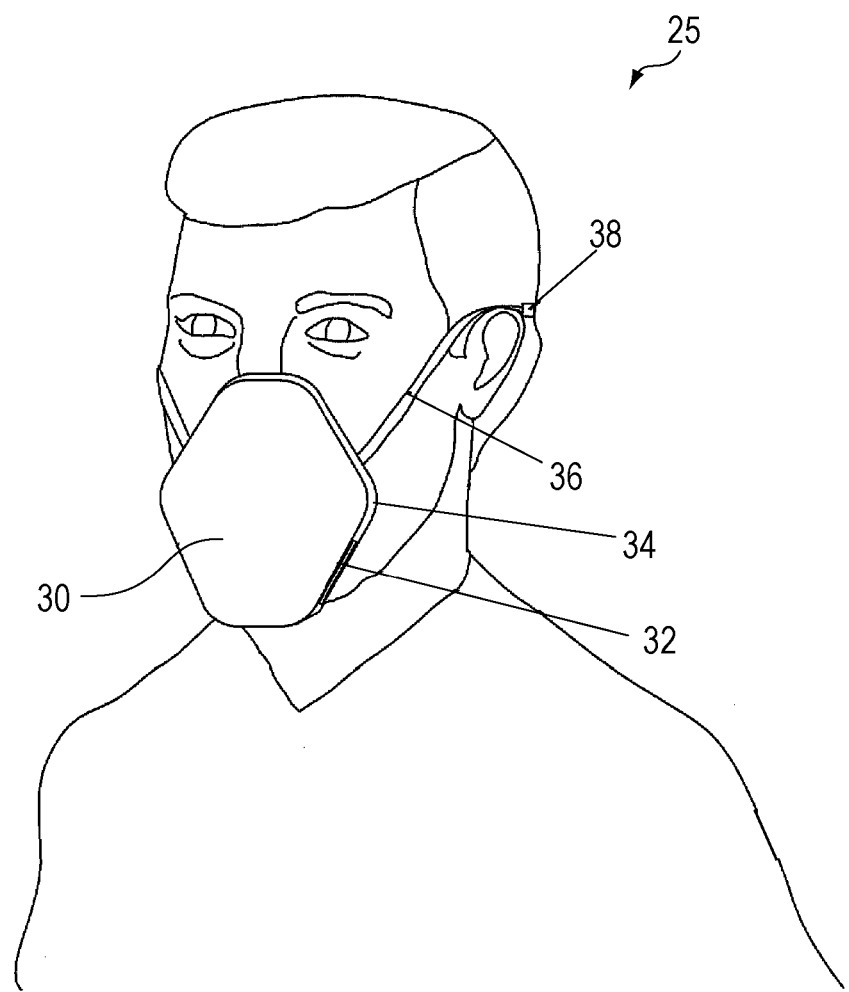
FIG. 2 illustrates a breathing apparatus according to embodiments of the invention.

FIG. 2 illustrates a breathing apparatus according to embodiments of the invention. Breathing apparatus 25 includes a facemask 30 which is sized and shaped to fit over a person's face, covering the mouth and/or nose of the wearer. Facemask 30 may be rigid or flexible and may include a flexible sealing ring 34 around the outside which forms a partial or full seal with the wearer's face. An opening 32 on at least one side of facemask 30 allows ambient air to flow into the facemask when the wearer inhales and allows exhaled air to flow out of the facemask when the wearer exhales. A string 36 or other suitable structure holds the facemask on the wearer's face. In some embodiments, the string 36 includes a power cord which connects ultraviolet (UV) LEDs in facemask 30 to a power source such as a rechargeable or disposable battery pack 38 attached to string 36 and worn behind the wearer's head, upper arm or waist.

Figure 3:
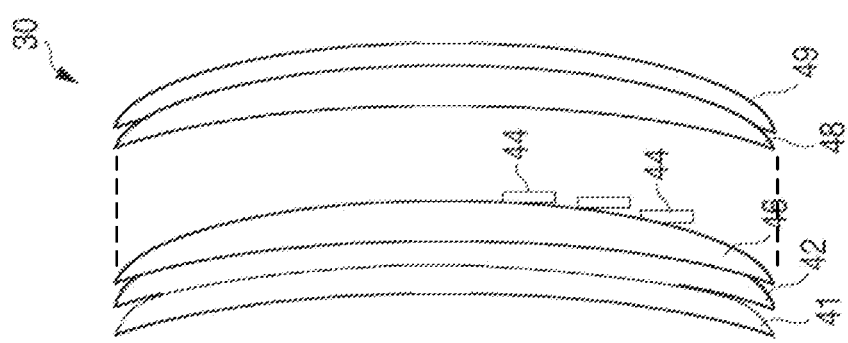
FIG. 3 is an exploded side view of the facemask illustrated in FIG. 2.

FIG. 3 is an exploded side view of facemask 30 of FIG. 2. A flow chamber in facemask 30 is formed by a support layer 42 and an outer shell 49. One example of a support layer 42 is illustrated in a plan view in FIG. 4. The support layer 42 may be, for example, a rigid or flexible circuit board on which one or more UV LEDs 44 are mounted. Wiring 54 may be formed on support layer 42 to electrically connect UV LEDs 44 to each other and to a power source such as a battery pack. Support layer 42 has an opening 37 located proximal to the wearer's nose and/or mouth, through which the wearer inhales and exhales. The surface of support layer 42 that forms a wall of the flow chamber may be coated or covered with any suitable UV-reflective material 46. Examples of suitable UV-reflective materials include but are not limited to metals or metal alloys, such as aluminum or palladium; oxides such as $SiO_2$ or $Al_2O_3$; metal-oxide hybrids; sulfate coatings; or UV reflective plastics, such as Teflon. The reflective coating 46 may be plated, sputtered, or evaporated directly on support layer 42, or the reflective coating may be a foil or a film attached to the surface of support layer 42 that forms the wall of the flow chamber.

The outer shell 49 of the flow chamber may be a rigid or flexible cover, such as a plastic or rubber cover. The surface of outer shell 49 that forms a wall of the flow chamber may be coated or covered with a UV-reflective material 48, which may be any of the materials formed by the methods described above in reference to reflective coating 46 on support layer 42.

The surface of the facemask 30 that touches the wearer's face may be covered with an optional fabric layer 41. The same or a different optional fabric layer may cover openings 32, for example to mechanically filter air in dusty environments. The same or a different optional fabric layer may cover opening 37, for example to contain liquid such as saliva or nasal fluid. Any of the optional fabric layers may be disposable or washable.

One or more UV LEDs 44 are located within the flow chamber. UV LEDs 44 may be any suitable devices that emit radiation at a wavelength that is able to disinfect the air flowing through the flow chamber. In some embodiments, UV LEDs 44 emit radiation with a peak wavelength less than 300 nm. In some embodiments, UV LEDs 44 are UVC LEDs, which emit light for example at a wavelength greater than 190 nm in some embodiments and less than 280 nm in some embodiments. In some embodiments, UV LEDs 44 are configured to emit light over broad angles, for example in a cone of at least 120°, such that UV radiation is emitted into as much of the volume in the flow chamber as possible. The emission pattern may be controlled through optics, lenses, or reflectors connected to the device structure of UV LEDs 44 or to packages in which the device structure of UV LEDs 44 are disposed, as is known in the art. UV LEDs 44 are disposed within the flow chamber and surrounded by reflective materials 46 and 48, such that little or no UV radiation is able to escape the flow chamber. The wearer of the breathing apparatus and the public are therefore exposed to little or no UV radiation from facemask 30.

Figure 4:
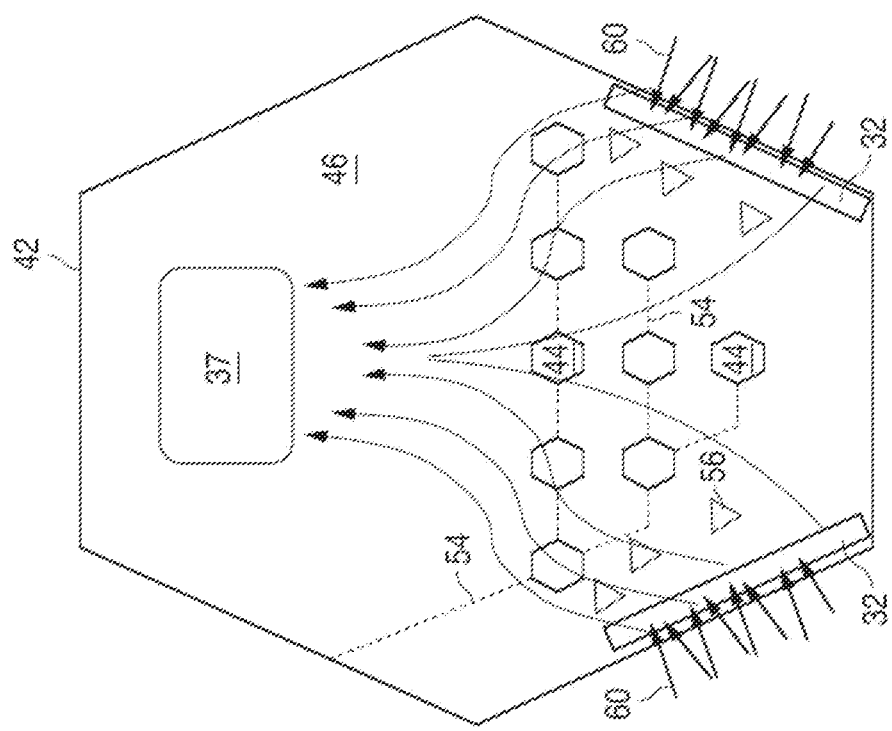
FIG. 4 illustrates an example of a support layer and air flow through a flow chamber in the facemask illustrated in FIG. 2.

FIG. 4 illustrates air flowing through the inside of the flow chamber. When the wearer inhales, ambient air 60 is drawn into the flow chamber through openings 32 located on a part of facemask 30 that is far from the wearer's nose and mouth. For example, openings 32 may be located on one or both sides of a lower part of the facemask 30, as illustrated in FIG. 4, and/or on the bottom of the facemask 30. Though two openings 32 are illustrated in FIG. 4, the shape, number, and size of openings 32 is not critical. The larger the openings 32, the easier it is to breathe through breathing apparatus 25. Openings 32 may be formed in support layer 42, in outer shell 49, or may be positioned at a seam between support layer 42 and outer shell 49.

Air 60 drawn in through openings 32 is drawn by the wearer's breathing toward one or more openings 37 located proximal to the wearer's nose and mouth. The air flows over UV LEDs 44 which are placed between the openings 32 to the outside and the opening 37 to the wearer's nose and mouth. Any pathogens in the air are killed by exposure to radiation emitted by UV LEDs 44, such that the air is disinfected by the radiation emitted by UV LEDs 44. Radiation emitted by UV LEDs 44 is reflected by reflective materials 46 and 48 such that all or nearly all of the flow chamber is filled with UV radiation. Accordingly, little or no air passes through the flow chamber without being exposed to UV radiation.

In some embodiments, one or more optional vanes or other structures 56 to create turbulence are disposed in the flow chamber, for example near openings 32 as illustrated in FIG. 4. Structures 56 mix the incoming air 60 and prevent laminar flow of the air, which may (1) effectively lengthen the trajectory of air within the flow chamber, and (2) allow air to pass closer to the surface of the LEDs where the radiation has the highest intensity, causing more exposure to stronger UV radiation, which may result in purer air. Alternatively, the flow chamber can be divided into several serpentine passages to extend the distance air must travel before reaching opening 37, causing more exposure to UV radiation, which may result in purer air. Serpentine passageways may be formed by forming passageway walls on one or both of support layer 42 and outer shell 49, such that when support layer 42 and outer shell 49 are pressed together to form facemask 30, sealed or nearly sealed passageways are formed.

FIG. 5A illustrates an alternative support layer 42. Instead of UV LEDs 44 being mounted directly on support layer 42 as in FIG. 4, UV LEDs 44 are disposed in individual reflective chambers 66. An individual reflective chamber is illustrated in FIG. 5B. When the wearer inhales, ambient air is drawn from the outside not through two large openings 32 as illustrated in FIG. 4, but through small openings 32 associated with each reflective chamber 66. The walls of reflective chamber 66 may be coated with reflective material, as described above in reference to support layer 42 and outer shell 49, shown in FIGS. 3 and 4. Purified air exits each reflective chamber 66 through an opening 64 in a side of each chamber 66 opposite the opening 32 through which ambient air 60 enters each chamber. Purified air 62 is drawn toward opening 37 by the wearer's breathing.

In some embodiments, an optional sensor such as a pressure sensor, flow sensor, or valve senses the direction of the airflow and therefore distinguishes the stage of the breathing cycle. One or more sensors may be placed, for example, near openings 32, near openings 37, or near both openings 32 and 37. Examples of suitable optional sensors include air flow meters or pressure sensors that are commercially available and used in devices such as spirometers and artificial lungs. UV LEDs 44 can be turned on or off depending on the stage of the breathing cycle. For example, for a wearer who is healthy, UV LEDs 44 can optionally be turned on only during the inhaling part of the breathing cycle, such that only inhaled air is purified. For a wearer who is sick, UV LEDs 44 can optionally be turned on only during the exhaling part of the breathing cycle, such that only exhaled air is purified. Activating UV LEDs 44 during only part of the breathing cycle may reduce the battery consumption of breathing apparatus 25.

In some embodiments, the same or an additional optional sensor such as a differential pressure sensor or flow sensor is disposed on one end of the flow chamber, for example over openings 32 or opening 37. The optional sensor senses the pressure or flow rate of the air passing through the flow chamber. The drive current of UV LEDs 44 may be adjusted in response to information detected by the optional sensor. For example, when breathing is rapid and labored, such as when the wearer is physically exerted (for example, a running paramedic), the current supplied to UV LEDs 44 can be increased proportionally with the airflow, increasing the power emitted by UV LEDs 44 to maintain the effectiveness of the disinfection reaction. When the wearer is resting peacefully (for example, a physician at her desk), the current supplied to UV LEDs 44 can be reduced to reduce battery consumption and potentially increase the lifetime of UV LEDs 44. In some embodiments, when the optional sensor indicates that full power is not needed, only some UV LEDs 44 or only portions of each UV LED 44 may be activated.

Figure 6:
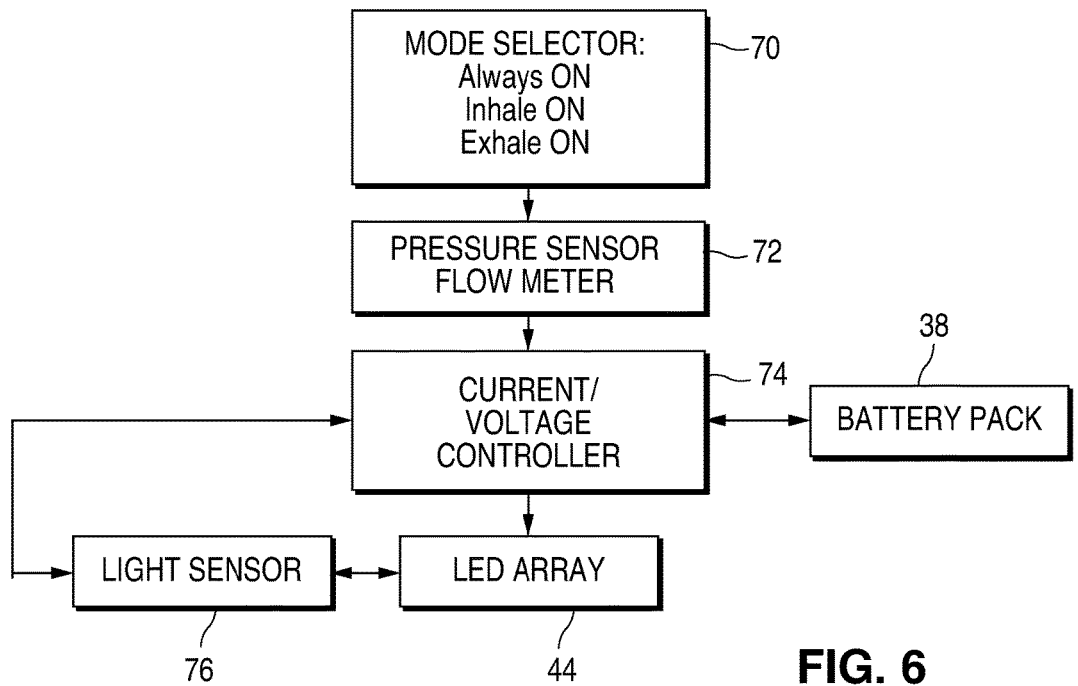
FIG. 6 illustrates electrical components suitable for controlling the UV LEDs in the breathing apparatus illustrated in FIG. 2.

FIG. 6 illustrates an example of electrical components for a control system for breathing apparatus 25. An optional mode selector 70 determines whether UV LEDs 44 are always on, are activated only during the inhale portion of the breathing cycle, or are activated only during the exhale portion of the breathing cycle. Mode selector 70 may be, for example, a user-activated switch. An optional sensor 72 such as a pressure sensor, flow meter, or valve may determine whether the wearer is inhaling or exhaling, and/or may determine the pressure and/or flow rate of air through the flow chamber. Information from mode selector 70 and sensor 72 may be provided to current/voltage controller 74, which supplies current to the array of UV LEDs 44 based on the information. Power is supplied to controller 74 by power source 38, which may be, for example, the battery pack illustrated in FIG. 2. An optional UV sensor 76 may indicate to controller 74 how much radiation is emitted from UV LEDs 44, and/or whether the UV LEDs 44 are in working order. UV sensor 76 may provide an alert when radiation emitted by UV LEDs 44 degrades beyond a preset threshold. The current/voltage controller circuit 74 may be embedded in an addition optional layer of material disposed within the mask, or in the same layer as UV LEDs 44 provided controller 74 does not materially interfere the flow of air. Mode selector switch 70 may be located anywhere convenient on the outer shell of the mask.

Figure 7:
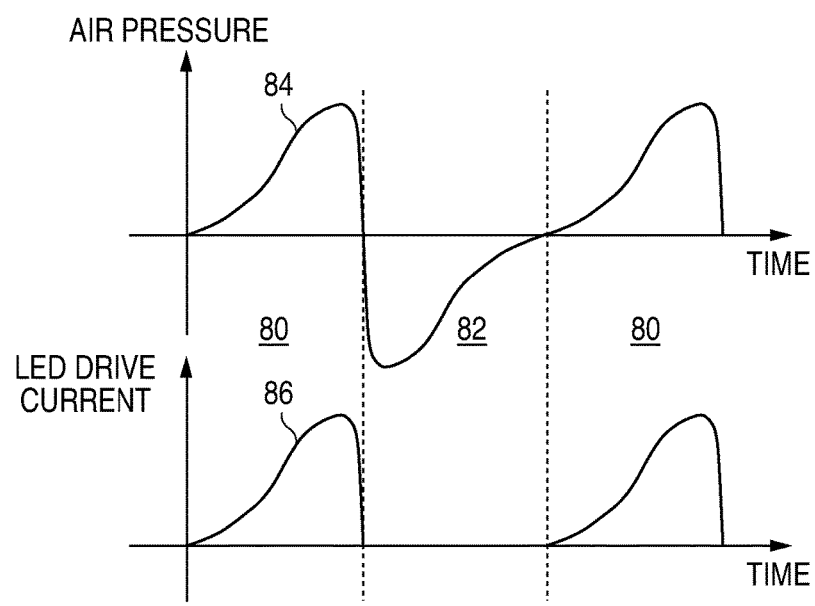
FIG. 7 illustrates one example of operation of the breathing apparatus of FIG. 2.

FIG. 7 illustrates one example of possible operation of the control system illustrated in FIG. 6. The top graph in FIG. 7 is a plot of air pressure as a function of time during normal breathing. Two inhales 80 and one exhale 82 are illustrated in FIG. 7. The bottom graph illustrates drive current supplied to UV LEDs 44 as a function of time. As is clear from the bottom graph, no drive current is supplied to UV LEDs 44 during exhale 82, indicating that mode selector 70 is set to active UV LEDs 44 only during the inhale portion of the breathing cycle. When the air pressure at sensor 72 indicates that the wearer is inhaling, controller 74 may activate some or all of the UV LEDs 44 in the flow chamber. In the operation illustrated in FIG. 7, controller 74 supplies drive current that is proportional to the air pressure. When air pressure reaches a peak 84 during the wearer's inhale, drive current supplied to UV LEDs 44 also reaches a peak 86. The proportional current/voltage output of the circuit can be achieved by amplifying pressure sensor signals (either current or voltage) by using current or voltage amplifiers commonly used in the electronics industry.

In some embodiments, pressure sensor/flow meter 72, current/voltage controller 74 and light sensor 76 are optionally connected to a data collection module. The module collects and stores respiratory data such as breathing volume, breathing rate, and chip performance data such as LED intensity and electrical driver status. The data may then be optionally transmitted via a transponder module such as those comprising a compact Bluetooth transceiver to another transceiver module not contained within the facemask itself, such as on a cellular phone or other mobile or stationary tracking device. The software on the mobile tracking devices may display such data for analysis for medical, maintenance or repair purposes, may issue failure or component replacement warnings, and/or may send commands to adjust the performance of various electronic components on the facemask.

Other functions such as digital recording play-back capabilities, decorative components, indicators, or fabrics may be added to the breathing apparatus.

Figure 1:
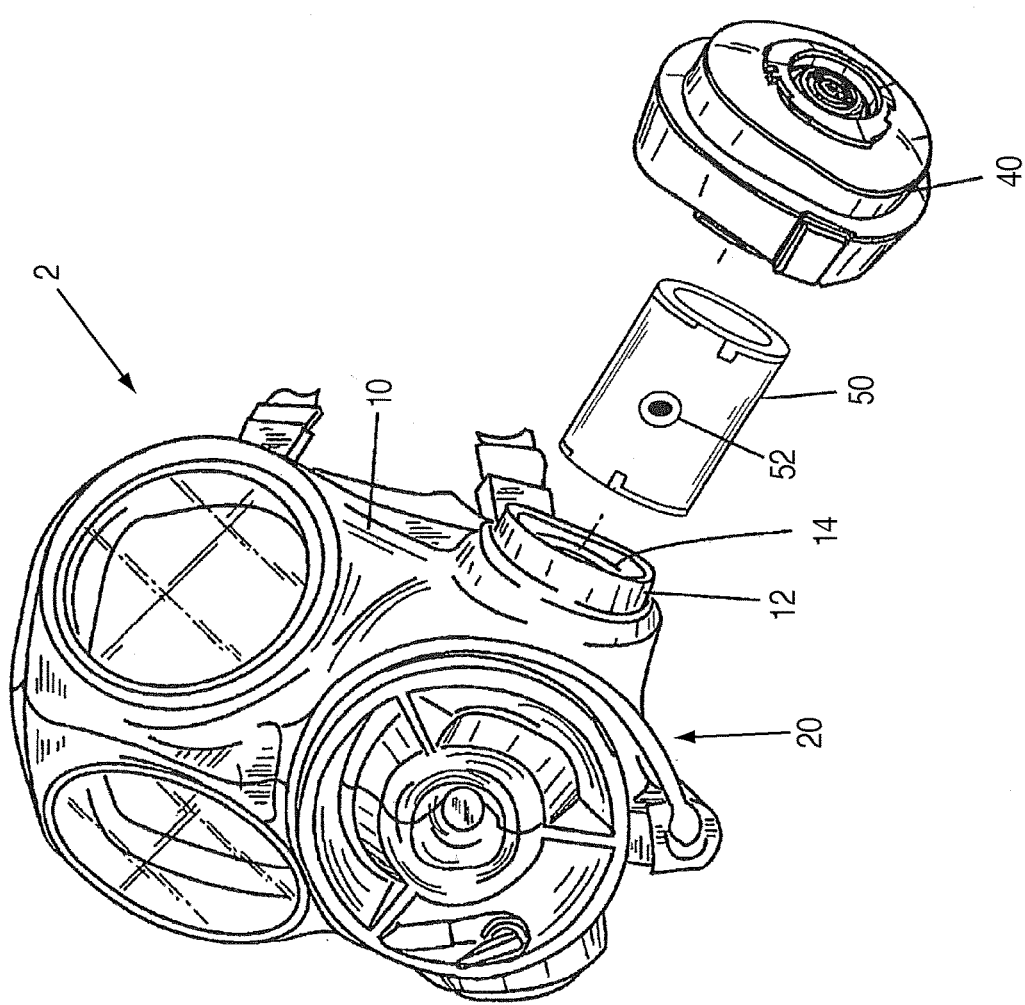
FIG. 1 illustrates a prior art chemical and biological protection mask.

The examples described above may offer advantages over conventional facemasks and the protection mask illustrated in FIG. 1. Embodiments of the invention provide direct air disinfection, which may be more effective at reducing the risk of respiratory infection, as compared to a conventional facemask. In embodiments of the invention, the flow chamber is not blocked with one or more layers of fabrics like a mechanical air filter. Also, unlike the protection mask illustrated in FIG. 1, embodiments of the invention do not require a completely sealed, face-tight fit in order to be effective. Accordingly, embodiments of the invention may be more comfortable for the wearer which may encourage use of the breathing apparatus, even during hot and humid weather.

Current state-of-the-art UVC LEDs with a size of, for example, 0.35×0.35×1.5 mm (L×W×H) may emit about 2-4 mW of UVC power at 40 mA. In addition, these LEDs can be operated in a pulsed or "flash" mode, reaching even higher intensity when supplied with higher current. Accordingly, during disinfection, the surface intensity of the UV LEDs may be at least $6\times10^6$ µW/cm² in some embodiments, at least $10^7$ µW/cm² in some embodiments (for example, a 0.5×0.5 mm² chip area at 25 mW per chip), and at least $5\times10^7$ µW/cm² in some embodiments (for example, a 1.2× 1.2 mm² chip area at 80 mW per chip). The surface intensity may be greater than 200 times the surface intensity of modern UV mercury bulbs. In some embodiments, the surface intensity refers to the intensity at the p-side emission area of the diode.

At such high intensity, 1 millisecond of exposure time may be sufficient to achieve 99%, or 2 Log reduction, of a typical influenza-A virus. The disinfection rate may be further improved by using multiple UV LEDs for example in a cluster or in any suitable arrangement, by using larger area single UV LEDs, or by using higher pulsed drive current.

In addition, UV LEDs, when turned ON, can reach peak power in less than one microsecond. Accordingly, there is essentially no delay to begin sterilization. In contrast, mercury bulbs may require several seconds, or longer, to reach peak output.

In some embodiments, the flow chamber is designed to maximize the utility of the surface space immediately adjacent to each LED. The flow chamber may be designed to force all or most of the air into the space immediately adjacent to the LEDs, where the intensity of UV light is highest.

Figure 8:
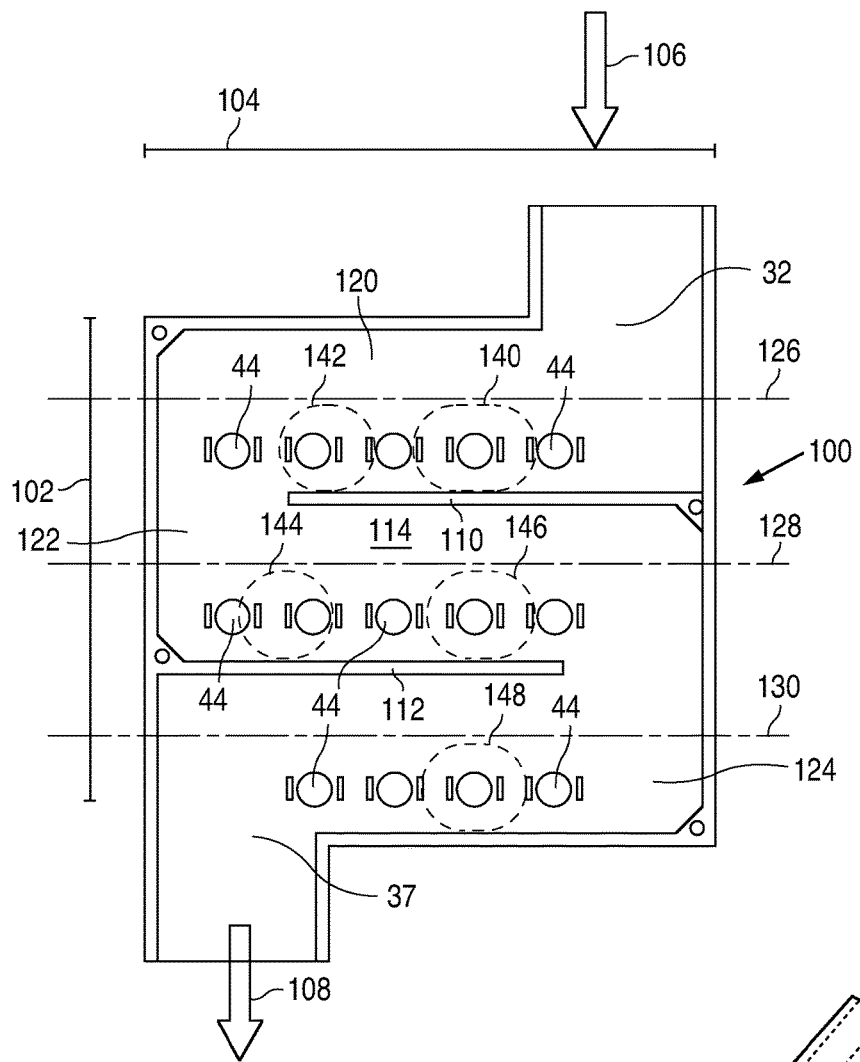
FIGS. 8 and 9 illustrate examples of a flow chamber including a serpentine passage.
Figure 9:
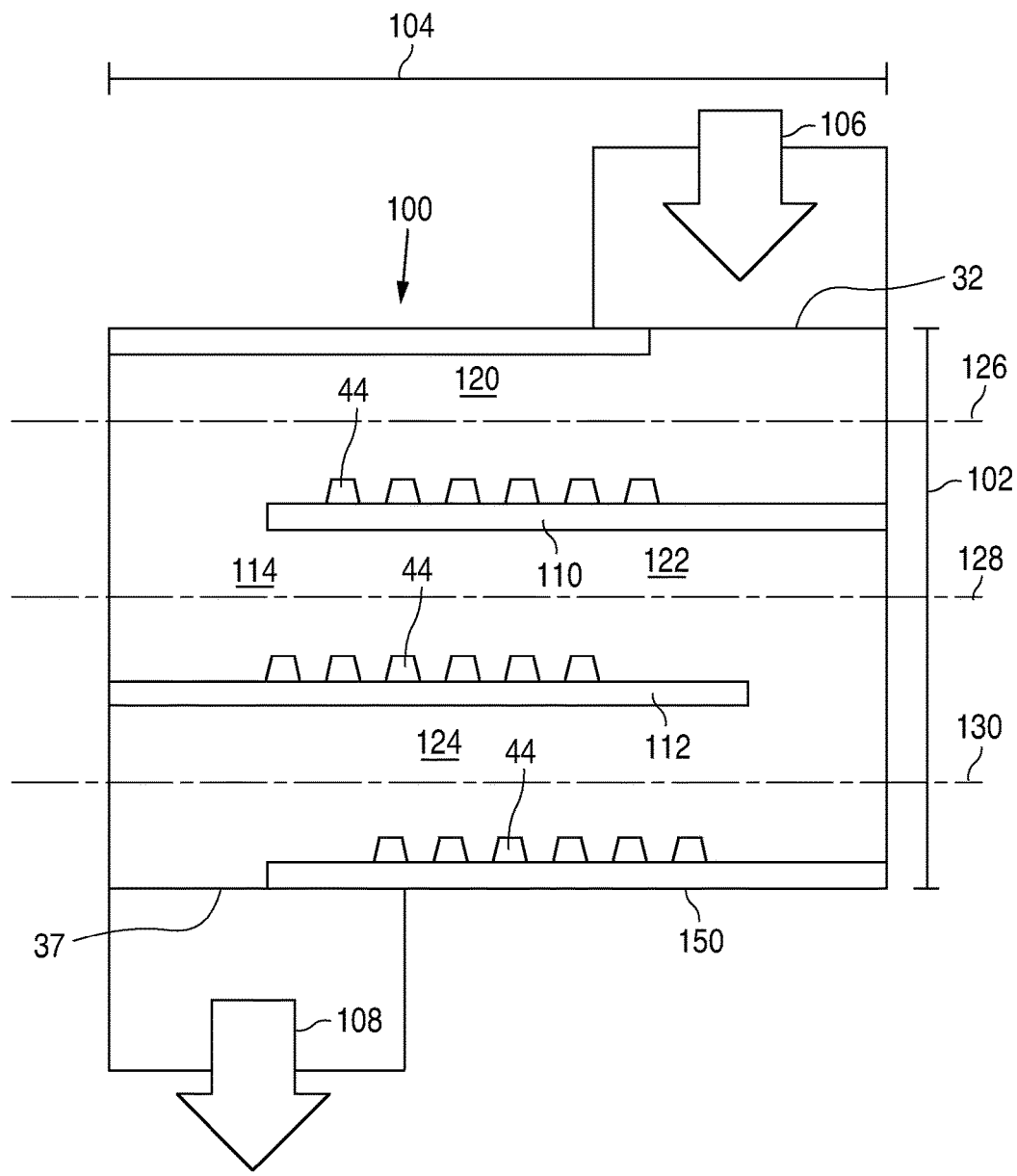

FIGS. 8 and 9 illustrate two examples of flow chambers 100. In each flow chamber, one or more openings 32 to the ambient air illustrated at the top of each figure, and one or more openings 37 proximal to the wearer are illustrated at the bottom of each figure. One opening 32 and one opening 37 are illustrated and described for economy of language. It is to be understood that there may be multiple openings 32 and multiple openings 37. The arrows 106 and 108 illustrate the flow of air when a wearer of the facemask inhales.

In order for the facemasks described herein to be widely adopted, the flow chambers are ideally made as compact and as light-weight as possible, without compromising the disinfection function, such that the facemask is comfortable to wear. The total volume of the flow chamber 100, and/or the volume of dimension 102 times dimension 104 times the thickness of the flow chamber 100 (the thickness extends out of the plane illustrated in the figures), may be no more than 80 $cm^3$ in some embodiments, no more than 50 $cm^3$ in some embodiments, no more than 30 $cm^3$ in some embodiments, no more than 20 $cm^3$ in some embodiments, no more than 10 $cm^3$ in some embodiments, and at least 0.5 $cm^3$ in some embodiments.

The dimension 102 of the flow chamber 100 is no more than 10 cm long in some embodiments, no more than 8 cm long in some embodiments, no more than 6 cm long in some embodiments, no more than 4 cm long in some embodiments, and at least 0.5 cm long in some embodiments. The dimension 104 of the flow chamber 100 is no more than 10 cm long in some embodiments, no more than 8 cm long in some embodiments, no more than 6 cm long in some embodiments, no more than 4 cm long in some embodiments, and at least 0.5 cm long in some embodiments. The thickness of flow chamber 100 is no more than 2 cm in some embodiments, no more than 1.5 cm in some embodiments, and no more than 1 cm in some embodiments, and at least 0.2 cm in some embodiments.

The flow chamber 100 may weigh no more than 10 grams in some embodiments, no more than 8 grams in some embodiments, no more than 6 grams in some embodiments, and at least 2 grams in some embodiments.

The flow chamber 100 has internal walls in order to form a serpentine passage 114. Two internal walls 110 and 112 are illustrated in FIGS. 8 and 9. More or fewer internal walls may be used, depending on, for example, the brightness of the UVC emitter. The width of the serpentine passage 114 formed by internal walls 110 and 112 may, for example, no more than 20 mm in some embodiments, no more than 15 mm in some embodiments, and at least 5 mm in some embodiments. The height of the serpentine passage 114 may be no more than 15 mm in some embodiments, no more than 10 mm in some embodiments, and at least 2 mm in some embodiments. In one example, the serpentine passage 144 is 14 mm wide and 8 mm high. Each UV LED 44 has an area about 2 mm×1.5 mm including a mount on which the UV LED is disposed, and an actual emission area of about 0.35×0.35 $mm^2$.

One or more LEDs 44 are disposed in the serpentine passage 114. Though 14 LEDs 44 are illustrated in FIGS. 8 and 18 LEDs 44 are illustrated in FIG. 9, more or fewer LEDs may be used. The serpentine passage 114 forces all or most of the air into the space immediately adjacent to the LEDs, where the intensity of UV light is highest.

As the wearer inhales and exhales, the air is forced into the fairly small serpentine passages by the inhaling pressure. The serpentine passages are narrow to force all air into the UV light. Accordingly, the flow speed is fast. The path length is selected to ensure a long enough exposure time. In one example, the total serpentine path length is at least 8 cm, in a serpentine passage with a cross sectional area of 100 $mm^2$.

The shape of the serpentine passage 114 may create regions of extreme turbulence. Five areas with very high turbulence, areas 140, 142, 144, 146, and 148 are illustrated in FIG. 8. For example, at a flow rate of at least 35 liters/min (a peak, instantaneous flow rate typical of a human breathing at rest), where the air flow is in the direction indicated by arrows 106 and 108, these areas may have a Reynold's number greater than 5000 in some embodiments, greater than 4000 in some embodiments, greater than 3000 in some embodiments, and no more than 12000 in some embodiments. One or more LEDs 44 may be disposed in the regions of high turbulence. When the air flow is turbulent, for example at Reynold's numbers greater than 4000, the air is sufficiently mixed that in these regions, most or all of the air will pass near the surface of the LEDs 44 for a sufficiently long time to kill any pathogens in the air. As described above, 1 millisecond exposure time is sufficient to kill 99% of a typical influenza-A virus. The serpentine passage 114 creates air flow that is sufficiently turbulent for efficient disinfection, without the use of artificial turbulence generators such as, for example, baffling on the sidewalls of the serpentine passage. The sidewalls of the serpentine passage may be smooth, though this is not required.

In the flow chamber 110 illustrated in FIG. 8, the serpentine passage 114 includes 3 sections, 120, 122, and 124. The center lines 126, 128, and 130 of each section are illustrated in FIG. 8. The regions with the most turbulence and/or aerosol density in each section, when air flows in the direction indicated by arrows 106 and 108, are below the center line or, in other words, across the center line from the sidewall where air enters the section. (Aerosol density is the number of viral particles per unit volume. Airborne bacteria/virus are considered aerosols, which can suspend in air for hours and are highly contagious. A droplet with a 3 µm diameter takes ~40 min to settle about 1.8 meters (human height). Droplets with diameters below 0.3 µm can stay aloft almost indefinitely.) In particular, the most turbulent regions 140 and 142 in section 120 are below center line 126, or across the center line 126 from opening 32, where air enters flow chamber 110. The most turbulent regions 144 and 146 in section 122 are below center line 128, or across the center line 128 from the junction of sections 120 and 122, where air enters section 122. The most turbulent region 148 in section 124 is below center line 130, or across the center line 130 from the junction of sections 122 and 124, where air enters section 124. LEDs 44 are placed in the most turbulent regions 140, 142, 144, 146, and 148. LEDs 44 in FIG. 8 are not centered in the serpentine passage 114; rather, they are placed off center, partially or entirely on one side of the center line of each section of serpentine passage 114.

The LEDs 44 in the embodiment illustrated in FIG. 8 are disposed on the top or bottom surface of the flow chamber, such that the tops of LEDs 44 are visible in the view illustrated in FIG. 8. Because UVC LEDs have significant side emission (for example, ~30% of total emissive power), in some embodiments the LEDs are elevated into the passage. In a device with an elevated LED, the side light may be directly used for disinfection, in comparison to device where the LEDs are sunk into cups, which require the use of reflectors to extract the side light, which may lead to optical loss. An added benefit to elevating LEDs into the passage is that doing so may generate additional turbulence for more uniform disinfection. The LEDs may be elevated by disposing the LEDs on submounts that are disposed on the top or bottom surface of the flow chamber. The submounts on which the LEDs are mounted may be, for example, at least 10 μm high in some embodiments, and no more than 5 mm high in some embodiments.

In some embodiments, the LEDs may be mounted with a twist in one or more of the x, y or z-axes relative to the flow chamber wall, to further enhance turbulence. (In the orientations illustrated in FIGS. 14A and 14B, the x- and y-axes are disposed in the plane of the bottom surface of the section, and the z-axis is perpendicular to the x- and y-axes.)

Figure 14A:
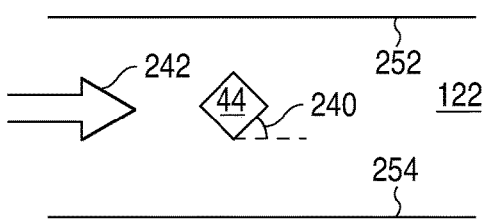
FIGS. 14A and 14B illustrate LEDs mounted at an angle relative to the direction of air flow.

FIG. 14A illustrates an LED mounted with a twist in the x- or y-axis. FIG. 14A is a top view of a square LED mounted at an angle 240 relative to the air flow direction 242. The LED 44 is shown disposed in section 122, though LED 44 could be in any section. The sidewalls 252 and 254 of a portion of section 122 are illustrated at the top and bottom of FIG. 14A.

Figure 14B:
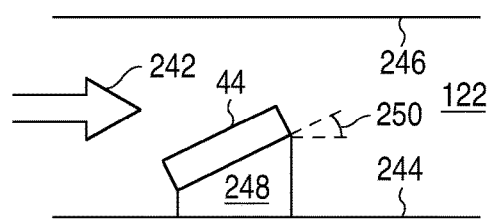

FIG. 14B illustrates an LED mounted with a twist in the z-axis. FIG. 14B is a side view of an LED 44 mounted in section 122 (though the LED illustrated in FIG. 14B could be mounted in any section). The top 246 and bottom 244 of a portion of section 122 are illustrated in the side view of FIG. 14B. LED 44 is mounted on a mount 248 which is angled 250 relative to the air flow direction 242.

Though both FIGS. 14A and 14B illustrate the LEDs twisted at an acute angle relative to the air flow direction, the LEDs may be mounted at any suitable angle.

The LEDs 44 in the embodiment illustrated in FIG. 9 are also disposed across the center lines 126, 128, and 130 of the sections 120, 122, and 124 of serpentine passage 114. The LEDs 44 in the embodiment illustrated in FIG. 9 are disposed on the sidewalls of internal walls 110 and 112, and on the sidewall of the wall 150 that forms one edge of the flow chamber 100. The sides of LEDs 44 are visible in the view illustrated in FIG. 9. The LEDs 44 are disposed on the walls of the flow chamber, rather than on the "floor" of the flow chamber as in FIG. 8, and therefore face the flow of air.

In both of the embodiments illustrated in FIGS. 8 and 9, the LEDs are placed in the regions with the most turbulence for air that is inhaled by the wearer of the facemask. Though air that is exhaled by the wearer will also pass over LEDs 44 and therefore be disinfected, disinfection is optimized for inhaled air, rather than exhaled air. The embodiments illustrated in FIGS. 8 and 9 are therefore best suited for applications where the wearer is to be protected from the environment.

In some embodiments, LEDs 44 may be placed in the flow chamber in regions with the most turbulence for air that is exhaled by the wearer of the facemask. For example, the LEDs may be placed on the opposite sides of center lines 126, 128, and 130. Such embodiments are best suited for applications where the environment is to be protected from the wearer.

In some embodiments, a flow sensor is disposed within the serpentine passage 114. The flow sensor may be disposed, for example, in an opening in a sidewall or in the "roof" of the serpentine passage. In some embodiments, the flow sensor is one or more microelectromechanical (MEMs) sensors. A MEMs sensor operates as follows: when no air flows over the MEMs sensor, or the air flow over the MEMs sensor is reduced, the sensor heats up. When air flow over the MEMs sensor is increased, the sensor cools down. A MEMs sensor is therefore a thermal sensor. In contrast, prior art pressure sensors are often mechanical. A MEMs sensor may be disposed within the flow chamber 110 to prevent wind-induced misreading. A MEMs sensor does not require the air flow to be stabilized or laminar in order to give an accurate reading.

Figure 10:
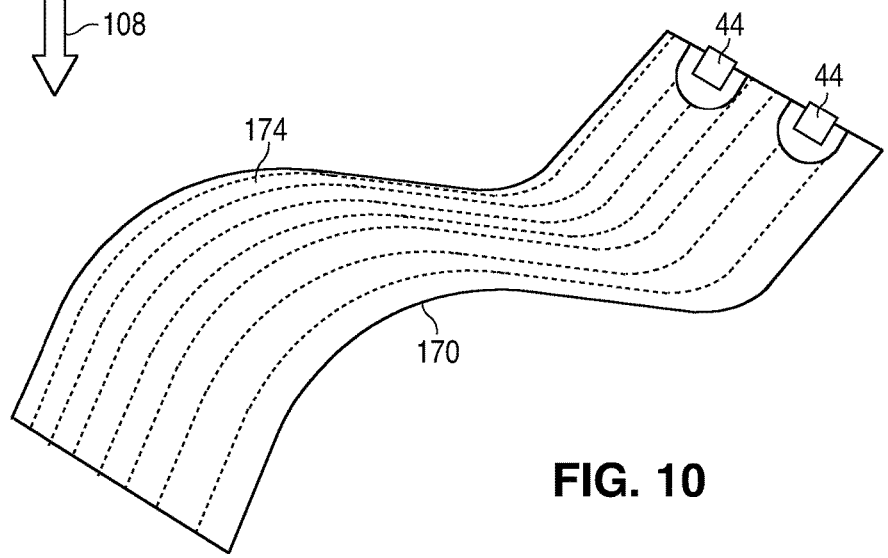
FIG. 10 illustrates a flexible waveguiding membrane.
Figure 11:
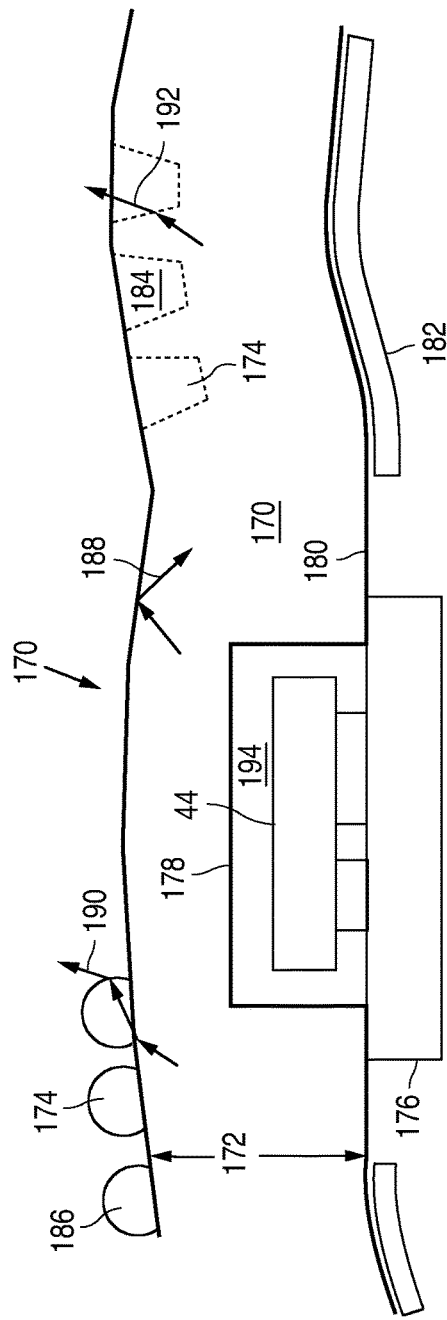
FIGS. 11 and 12 are cross sections of portions of flexible waveguiding membranes.
Figure 12:
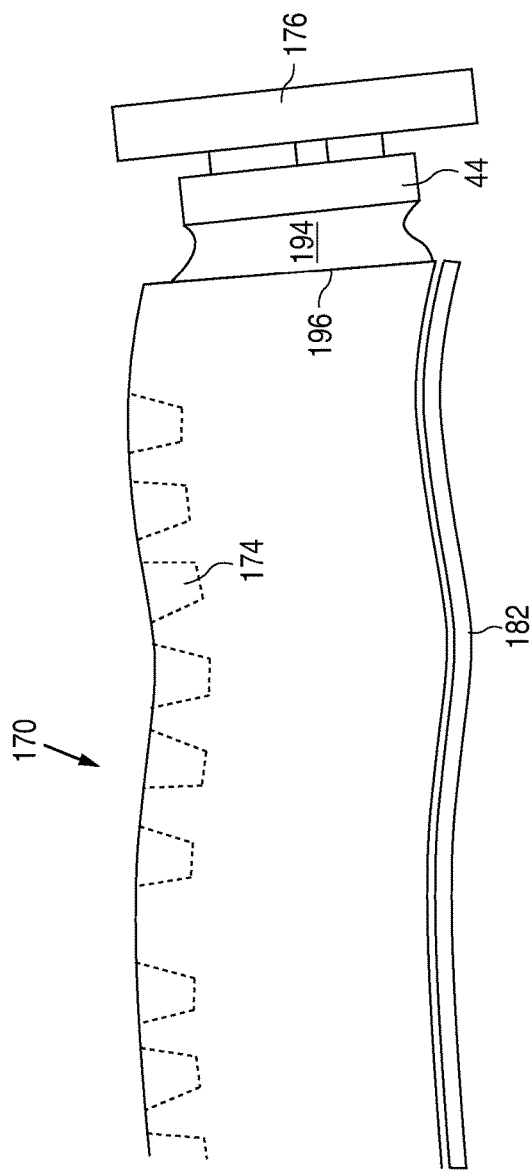
Figure 13:
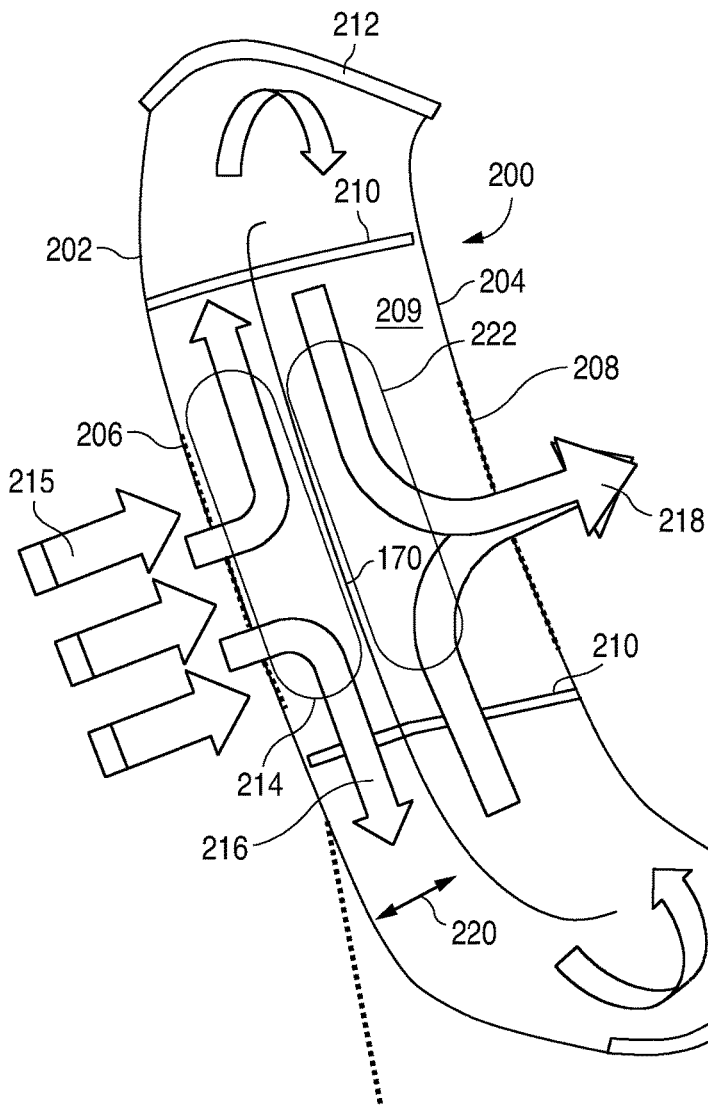
FIG. 13 is a cross sectional view of a facemask incorporating a flexible waveguiding membrane.

FIG. 10 illustrates a flexible waveguiding membrane for a facemask. FIGS. 11 and 12 are cross sections of portions of two examples of a flexible waveguiding membrane. FIG. 13 illustrates a facemask including a flexible waveguiding membrane.

The flexible membrane 170 of FIG. 10 may be sized to fit within a facemask, as described in reference to FIG. 13. The flexible membrane 170 may be any suitable material such as, for example, plastic such as polyvinyl chloride, or silicone, especially silicones with enhanced UV transmission. One or more UV LEDs 44 are optically coupled to membrane 170, such that light is extracted from the UV LEDs 44 into the membrane 170. UV LEDs 44 may be disposed on an edge of membrane 170, as illustrated in FIG. 10, or in any other suitable location. The membrane 170 serves as an optical waveguide for UV light. The LEDs may be mounted inside a cavity in the membrane, as illustrated in FIG. 11, with or without an angle relative to the edge of the membrane, (such as, for example, either or both of the angles illustrated in FIGS. 14A and 14B), to enhance optical coupling, especially to better capture the side light.

Multiple surface emission features 174 are formed on the surface of or within the membrane 170. For example, the surface emission features 174 may be holes or protrusions formed by laser-drilling, molding, printing, stamping, or any other suitable technique. The shapes of the holes and/or protrusions can be pyramidal, faceted, or any other suitable shape. The optimum size, depth or height, and spacing of the surface emission features 174 may be determined by the wavelength used, and/or the intensity desired. The features may be at least 50 nm wide in some embodiments, no more than 10 μm wide in some embodiments, at least 10 μm wide in some embodiments, and no more than 50 μm wide in some embodiments. The features may be at least 50 nm high or deep in some embodiments, no more than 10 μm high or deep in some embodiments, at least 5 μm high or deep in some embodiments, and no more than 50 μm high or deep in some embodiments. The features may be at least 20 nm from a nearest neighbor in some embodiments, no more than 150 μm from a nearest neighbor in some embodiments, at least 20 μm from a nearest neighbor in some embodiments, and no more than 50 μm from a nearest neighbor in some embodiments. In one example, features 174 are printed hemispheres 30 μm in diameter, with a nearest-neighbor center spacing of 10 μm. The features 174 may be arranged in any suitable arrangement, including a square, hexagonal, triangular, Archimedes, fractal, or any other suitable array, linear arrays as illustrated in FIG. 10, a random or quasi-random arrangement, or any other suitable arrangement. The features 174 are placed in areas on the flexible membrane where UV light is to be extracted from the membrane.

FIGS. 11 and 12 are partial cross sections of two examples of flexible membrane 170. One or more UV LEDs 44 are positioned at one or more ends 196 of the membrane 170, as illustrated in FIG. 12, or embedded within a cavity 178 formed in one or more major surfaces 180 of the membrane 170, as illustrated in FIG. 11. The UV LEDs 44 may be electrically and mechanically connected to a circuit board 176 or any other suitable structure. The UV LEDs 44 may be optically coupled to the waveguiding membrane 170 through an index-matching material 194, which may be silicone or any other suitable material. In some embodiments, the index-matching material 194 has an index of refraction n>1.3 at 280 nm. The thickness 172 of the membrane should be similar to the emission area of the UV LED 44, to allow better capturing of the emitted light. The thickness 172 of membrane 170 is 1 mm in some embodiments, at least 0.5 mm in some embodiments, no more than 1.5 mm in some embodiments, at least 0.2 mm in some embodiments, and no more than 8 mm in some embodiments.

In the membranes illustrated in FIGS. 11 and 12, light extraction features 174 are formed on one major surface of the membrane 170. FIGS. 11 and 12 illustrate features that are holes 184 extending from a surface of the membrane 170 into the membrane, toward the center of the membrane. FIG. 11 illustrates features that are protrusions 186 that are formed on top of a surface of the membrane. Light ray 188 illustrates how light is waveguided within the membrane 170. Light ray 190 illustrates how light is extracted from the membrane by a protrusion feature 174. Light ray 192 illustrates how light is extracted from the membrane by a hole feature 174.

In some embodiments, a reflective layer 182 is disposed on all or a portion of the other major surface of the membrane 170. The reflective layer 182 may be a reflective coating such as a metal, reflective paint, or any other suitable reflective material. In some embodiments, light extraction features 174 are formed on both major surfaces of the membrane 170. UV light is extracted from membrane 170 wherever features 174 are formed.

FIG. 13 illustrates a facemask incorporating a flexible membrane, as described above. The facemask includes an outer shell 202 with at least one opening or partially air-permeable area 206, and an inner shell 204 (closer to the face) with at least one opening or partially air-permeable area 208. The outer and inner shells may be fabric, plastic, or any other suitable material. The outer and inner shells may be the same material, though this is not necessary. The inner and outer shells form a disinfection enclosure 209, with the perimeter 212 sealed by stamping or welding of non-woven fabrics, or other processes for plastics.

Sandwiched between the inner and outer shells 202 and 204 inside the disinfection chamber 209 is a flexible waveguiding membrane 170, as described above. The membrane 170 may be held in place by any suitable means, such as, for example, flexible plastic scaffolding 210 or protrusions on the membrane. The flexible membrane 170 is separated 220 from the inner wall of the outer shell 202 by about 1 mm in some embodiments, at least 0.1 mm in some embodiments, and no more than 5 mm in some embodiments. The spacing between the flexible membrane and the inner wall of the inner shell 204 may be the same as the outer shell 202, though this is not required. In some embodiments, the spacing between the flexible membrane and the inner and outer shells is greater in a mask intended for an adult than in a mask intended for a child, to accommodate greater flow rates.

The light extraction features 174 may be formed on flexible membrane 170 such that UV light leaks from the membrane 170 into region 214, which is between the outer shell 202 and the membrane 170. Air 215 inhaled through the air permeable area 206 of the outer shell 202 encounters UV light region 214 and is disinfected. The air is pulled 216 around membrane 170 and out 218 through the air permeable area 208 of inner shell 204 by the mask wearer's inhalation.

The facemask 200 as illustrated and described above is arranged to disinfect primarily air that is inhaled by the facemask wearer. The light extraction features on the flexible membrane 170 may be formed such that UV light leaks from membrane 170 into region 222, which is between flexible membrane 170 and inner shell 204. Such a facemask disinfects primarily air that is exhaled by the facemask wearer. The flexible membrane 170 can be configured such that UV light is leaked into both regions 214 and 222, such that the facemask disinfects both inhaled and exhaled air. Additional sensors, controllers and data collection and transmission modules as described above may also be used in the embodiments illustrated in FIG. 13 and described in the accompanying text.

Having described the invention in detail, those skilled in the art will appreciate that, given the present disclosure, modifications may be made to the invention without departing from the spirit of the inventive concept described herein. In particular, different features and components of the different devices described herein may be used in any of the other devices, or features and components may be omitted from any of the devices. Therefore, it is not intended that the scope of the invention be limited to the specific embodiments illustrated and described.

What is being claimed is:

1. A breathing apparatus, comprising:
    a facemask portion sized to cover a lower portion of a wearer's face, the facemask portion comprising:
    a flow chamber comprising:
        a conduit, comprising:
            a first opening disposed near a first end of the flow chamber;
            a second opening disposed near a second end of the flow chamber; and
            at least two internal walls that form a serpentine passage disposed between the first opening and the second opening, the serpentine passage including at least a first section in communication with the first opening, a second section connected by a first U-shaped bend with the first section, and a third section connected by a second U-shaped bend with the second section;
    at least one light emitting diode configured to emit light having a peak wavelength in the ultraviolet range disposed in one of the first, the second, and the third sections of the conduit, wherein;
    the at least one light emitting diode is disposed off center relative to a centerline of the one of the first, the second, and the third sections; and
    the centerline is parallel to one of the two internal walls.

2. The breathing apparatus of claim 1 wherein the at least one light emitting diode is disposed in a region of maximum air turbulence or aerosol density in the serpentine passage.

3. The breathing apparatus of claim 1 wherein the at least one light emitting diode is disposed on a sidewall forming the serpentine passage.

4. The breathing apparatus of claim 1 wherein the at least one light emitting diode is disposed on a floor of the flow chamber.

5. The breathing apparatus of claim 1 further comprising:
a thermal sensor, wherein the thermal sensor is configured to detect a flow rate of air through the serpentine passage; and
a controller coupled to the thermal sensor and the at least one light emitting diode, wherein the controller is configured to supply current to the at least one light emitting diode based on information received from the thermal sensor.

6. The breathing apparatus of claim 5 wherein the thermal sensor is a MEMS sensor.

7. The breathing apparatus of claim 1, further comprising a plurality of light emitting diodes, including the at least one light emitting diode, all disposed below the centerline and away from the sidewall where air enters the section.

8. The breathing apparatus of claim 1, wherein the flow chamber has a volume no more than 80 cm$^3$.

9. The breathing apparatus of claim 1, wherein the at least one light emitting diode is disposed below the centerline and away from a wall where air enters the one of the first, the second, and the third sections.

10. A breathing apparatus, comprising:
a facemask portion sized to cover a lower portion of a wearer's face, the facemask portion comprising:
 a disinfection chamber disposed between an inner shell and an outer shell, each of the inner shell and the outer shell having at least one opening;
 an optical waveguide comprising a transmissive membrane and light extraction features, the transmissive membrane comprising a solid sheet, the light extraction features comprising holes extending from a surface of the transmissive membrane or protrusions formed on top of the surface of the transmissive membrane; and
 at least one light emitting diode coupled to the transmissive membrane, the at least one light emitting diode being configured to emit light having a peak wavelength in the ultraviolet range, the light emitted by the at least one light emitting diode being waveguided within the transmissive membrane and extracted from the transmissive membrane by the light extraction features.

11. The breathing apparatus of claim 10 wherein the light extraction features are disposed on a first major surface of the transmissive membrane and a reflective material is disposed on at least a portion of a second major surface of the transmissive membrane.

12. The breathing apparatus of claim 10 where the at least one light emitting diode is disposed on an edge of the transmissive membrane.

13. The breathing apparatus of claim 10 wherein the transmissive membrane is flexible.

14. The breathing apparatus of claim 10 wherein the at least one light emitting diode is disposed in cavity formed in a surface of the transmissive membrane opposite the light extraction features.

15. The breathing apparatus of claim 10 wherein the transmissive membrane is one of plastic and silicone.

16. The breathing apparatus of claim 10 wherein the transmissive membrane is UV transparent.

* * * * *